United States Patent [19]
Kovalchick et al.

[11] Patent Number: 6,009,744
[45] Date of Patent: Jan. 4, 2000

[54] SYSTEM AND METHOD FOR HIGH VOLTAGE LEAK DETECTION

[75] Inventors: Matthew J. Kovalchick, Front Royal, Va.; Shao Chi Yang, Gaithersburg, Md.

[73] Assignee: Hoppmann Corporation, Chantilly, Va.

[21] Appl. No.: 09/041,127

[22] Filed: Mar. 12, 1998

Related U.S. Application Data

[60] Provisional application No. 60/040,433, Mar. 12, 1997.

[51] Int. Cl.[7] .......................... G01R 31/12; G01M 3/40; G01N 27/70
[52] U.S. Cl. .................... 73/40; 73/49.3; 324/536; 324/557
[58] Field of Search ................. 73/40, 49.2, 49.3, 73/41; 324/557, 558, 559, 71.1, 536, 551, 554

[56] References Cited

U.S. PATENT DOCUMENTS

| | | | |
|---|---|---|---|
| 3,739,332 | 6/1973 | Martinez | 340/37 |
| 4,125,805 | 11/1978 | Nagamatsu et al. | 324/54 |
| 4,325,910 | 4/1982 | Jordan | 422/64 |
| 5,198,773 | 3/1993 | Latta | 324/464 |
| 5,455,507 | 10/1995 | Horenstein | 324/557 |
| 5,510,718 | 4/1996 | Enderby | 324/536 |
| 5,535,618 | 7/1996 | Konieczka | 73/49.3 |

FOREIGN PATENT DOCUMENTS

3915797A1  11/1989  Germany.

*Primary Examiner*—Hezron Williams
*Assistant Examiner*—J. David Wiggins
*Attorney, Agent, or Firm*—Birch, Stewart, Kolasch & Birch, LLP

[57] ABSTRACT

A system and method for detecting leakage of a part, includes a controller for generating a start command, a voltage generating circuit for generating at least one high voltage pulse signal in response to the start command, at least one testing station including first and second probes for placing a non-conductive part therebetween and for applying the at least one high voltage pulse signal to the non-conductive part, and an inductive detector detecting current from one of the first and second probes. The inductive detector generates a detection signal in response to the detection and transmits it to the controller. The controller compares the detection signal with a reference signal and determines any presence of leaks in the non-conductive parts based on the comparison result.

20 Claims, 4 Drawing Sheets

6,009,744

SYSTEM AND METHOD FOR HIGH VOLTAGE LEAK DETECTION

This application claims priority on provisional application Serial No. 60/040,433 filed on Mar. 12, 1997, the entire contents of which are hereby incorporated by reference.

BACKGROUND OF THE INVENTION

1. Field of the Invention

The present invention relates to a leak detection system for work pieces and, more particularly, to a system and method for detecting leaks in non-conductive work pieces using high voltage and working at high speed.

2. Description of the Related Art

When work pieces, such as plastic parts, are manufactured, they are tested to ensure that no holes or leaks are formed therein. In the past, pressured air was applied to the plastic parts to detect such leakage. If air were detected to leak from the plastic parts, the parts were rejected as having defects. However, this process is time consuming and inefficient, especially when the system requires a high speed detection of several hundred parts per minute.

SUMMARY OF THE INVENTION

It is an object of the present invention to provide a leak detection system and method that detects leaks at high speed without the use of pressurized air.

It is another object of the present invention to provide a leak detection system and method that detects leaks using high voltage and inductive sensing.

It is still another object of the present invention to provide a leak detection system and method that overcomes problems and disadvantages of conventional leak detection systems.

Briefly described, the present invention is directed to a system for detecting leakage of a part, including a controller for generating a start command; a voltage generating circuit for generating at least one high voltage pulse signal in response to the start command; at least one testing station including first and second probes for placing a non-conductive part therebetween and for applying the at least one high voltage pulse signal to the non-conductive part; and an inductive detector detecting current from one of the first and second probes, the inductive detector generating to the controller a detection signal in response to the detection, the controller comparing the detection signal with a reference signal and determining presence of leaks in non-conductive parts.

Moreover, the preset invention is directed to a method for detecting leakage of a part, including the steps of generating a start command; generating at least one high voltage pulse signal according to the start command; applying the at least one high voltage pulse signal to a non-conductive part positioned between first and second probes of at least one testing station; inductively detecting current from one of the first and second probes and generating a detection signal; and comparing the detection signal with a reference signal to detect leaks in non-conductive parts.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
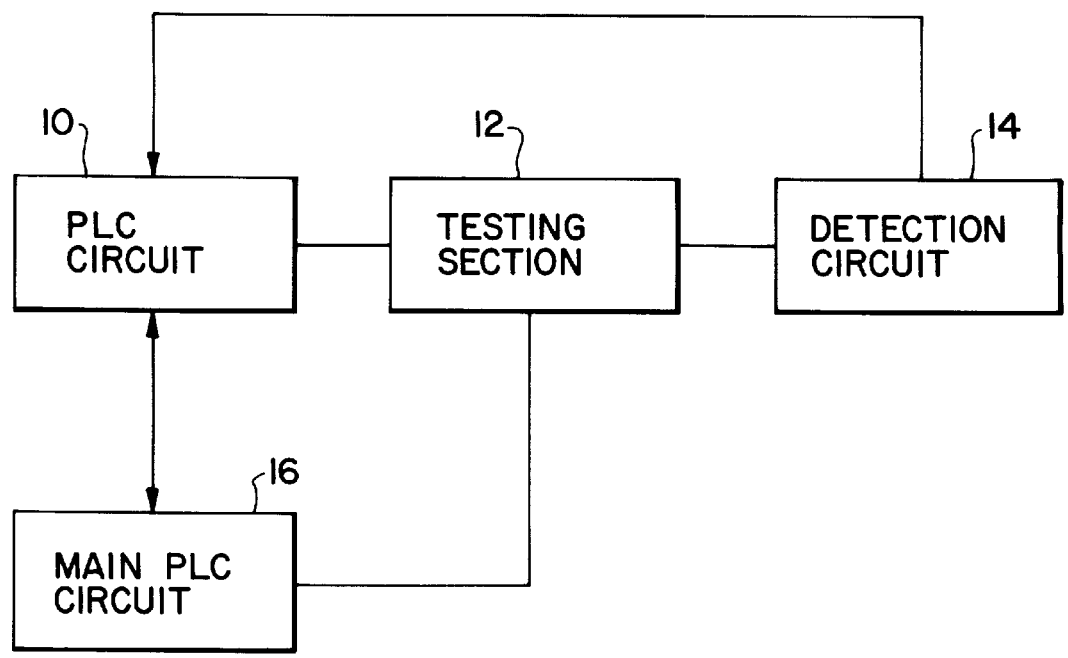
FIG. 1 is a block diagram of a high voltage leak detection system according to the embodiments of the present invention.

Referring in detail to the drawings and with particular reference to FIG. 1, the high voltage leak detection system according to the embodiments of the present invention includes a programmable logic controller (PLC) circuit 10, a testing section 12, a detection circuit 14, and a main PLC circuit 16, all coupled to each other.

Generally, the PLC circuit 10 generates a start command to the testing section 12 which generates one or more high voltage pulses. These high voltage pulses are applied to a work piece or testing part and the detection circuit 14 monitors leakage current from the testing part. The leakage current detected by the detection circuit 14 is processed and transmitted to the PLC circuit 10. The PLC circuit 10 compares the detection signal from the circuit 14 with a reference signal and outputs the comparison results to the main PLC circuit 16. If the comparison results indicate that the part is defective, the main PLC circuit 16 controls a testing assembly to reject the part. Otherwise, the part is moved from the testing assembly and stored as having passed the leak inspection.

Figure 2:
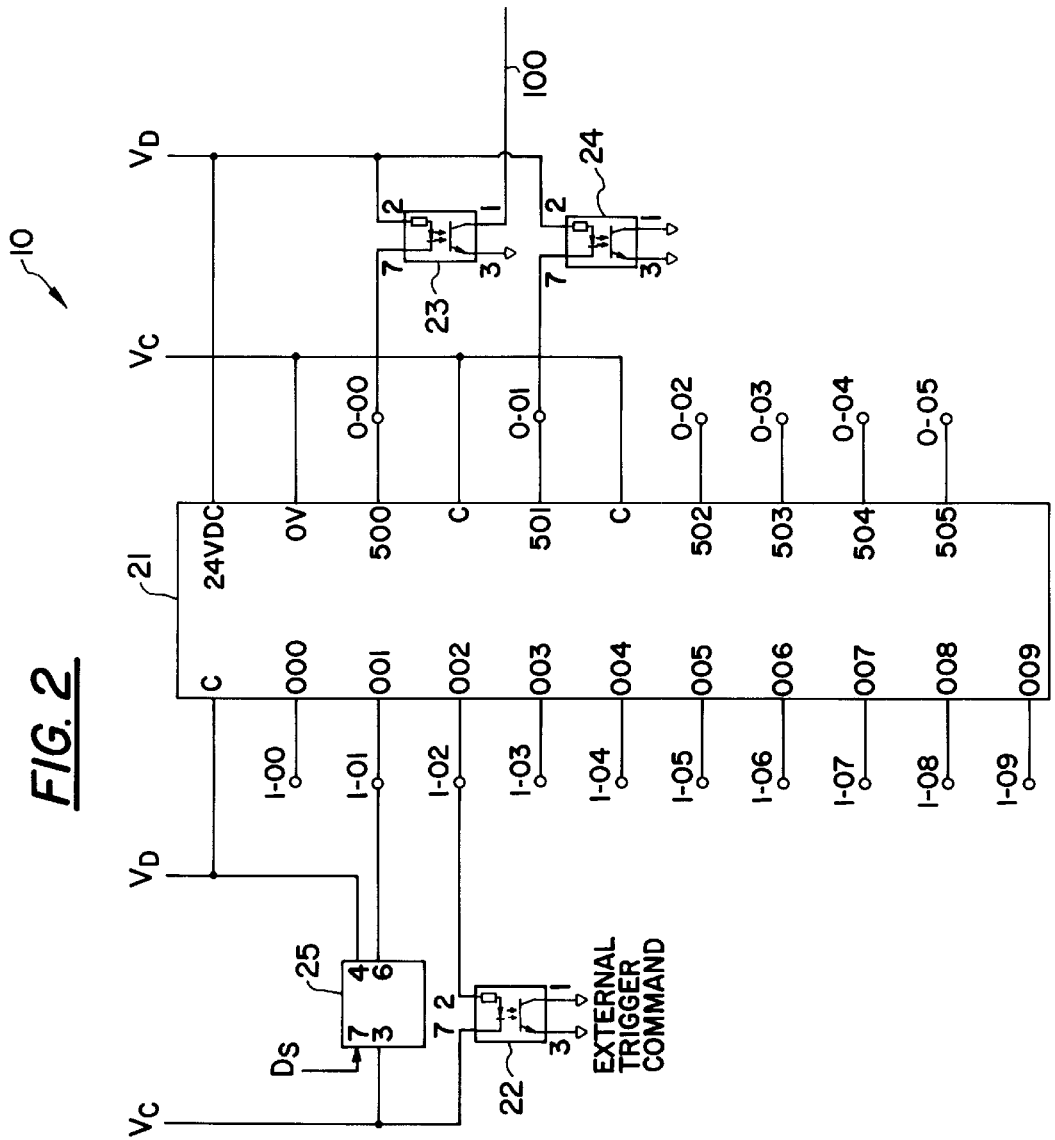
FIG. 2 is a circuit diagram of a left-hand part of a circuit used in the high voltage leak detection system of FIG. 1, with line 100 being connected to line 100 in FIG. 3.

FIG. 2 shows a detailed circuit diagram of the PLC circuit 10 of FIG. 1 according to the embodiments of the present invention.

As shown in FIG. 2, the PLC circuit 10 includes a PLC 21 for processing and transmitting signals input thereto to appropriate locations according to the programmed logic, a plurality of optical couplers 22, 23 and 24 for isolating voltage signals input thereto, and a monostable trigger circuit 25 for controlling the pulse duration of an input signal. The monostable trigger circuit 25 receives a detection signal Ds from the detection circuit 14 and adjusts the duration of the detection signal Ds to provide a more reliable detection signal to the PLC 21. The PLC circuit 10 is connected to a common voltage Vc and a voltage source VD for supplying, e.g. +24 VDC, to the PLC 21 and other elements. The PLC 21 may be, e.g., a Keyence KV-16T type, which has a scan time of 0.2–0.4 ms, but other suitable controllers could be used.

Figure 3:
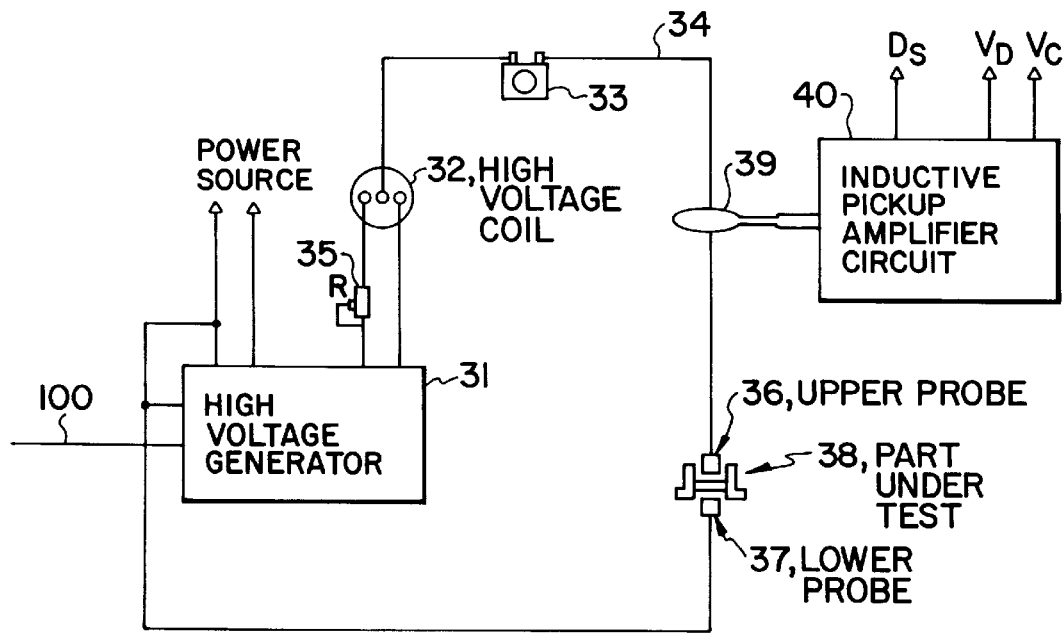
FIG. 3 is a circuit diagram of a right-hand part of the circuit used in the detection system of FIG. 1, with line 100 being connected to line 100 in FIG. 2.

As shown in FIG. 3, the testing section 12 includes a high voltage generator 31, a high voltage coil 32, a spark gap member 33, at least one testing station 51 having upper and lower probes 36 and 37 for holding a part 38 to be tested therebetween, and a high voltage cable 34 for providing connections therebetween.

The high voltage generator 31 includes a power connection and a coil connection. Through the power connection, the generator 31 receives power to generate a high voltage of about 40 KV. The high voltage generator 31 may be, e.g. a MSD type high voltage generator, well known in the automobile industry to generate 40 KV. The high voltage coil 32 functions as an ignition coil and the voltage generated by the generator 31 is adjusted by controlling a variable resistor 35. The variable resistor or potentiometer 35 is adjusted to control the level of high voltage applied to the testing parts. In the present case, the variable resistor 35 adjusts the voltage level to about 10–20 KV so that voltage spikes (pulses) of 10–20 KV are applied to the testing parts; however, other spike levels may be used according to the appropriate performance and output requirements.

Figure 4:
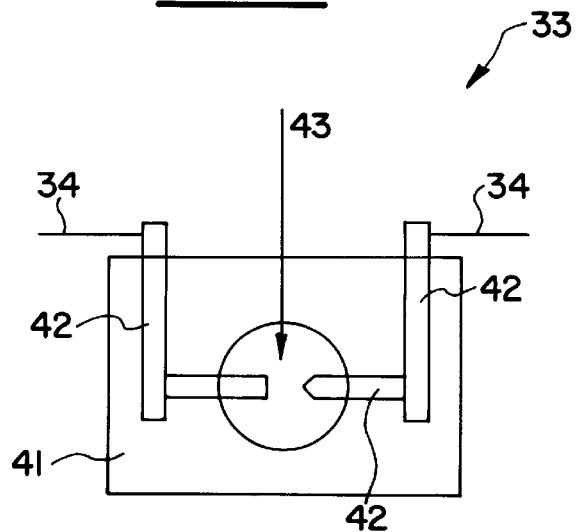
FIG. 4 is a side view of a spark gap member used in the circuit of FIG. 3 according to the embodiments of the present invention.

The testing section 12 further includes the spark gap member 33 as shown in, e.g., FIG. 4. The spark gap member 33 includes metal bars 42 located within a plastic housing 41, and an air gap 43 formed between two metal bars 42. When a high voltage is applied to the spark gap member 33, an electric arc appears between the two metal bars 42 in the air gap 43. Therefore, the spark gap member 33 functions as a visual indicator to the user that the high voltage pulses are generated and applied to the testing parts. Furthermore, the spark gap member 33 functions as a small capacitor to enhance the performance of the detection system and the application of the high voltage to the testing parts.

Figure 6:
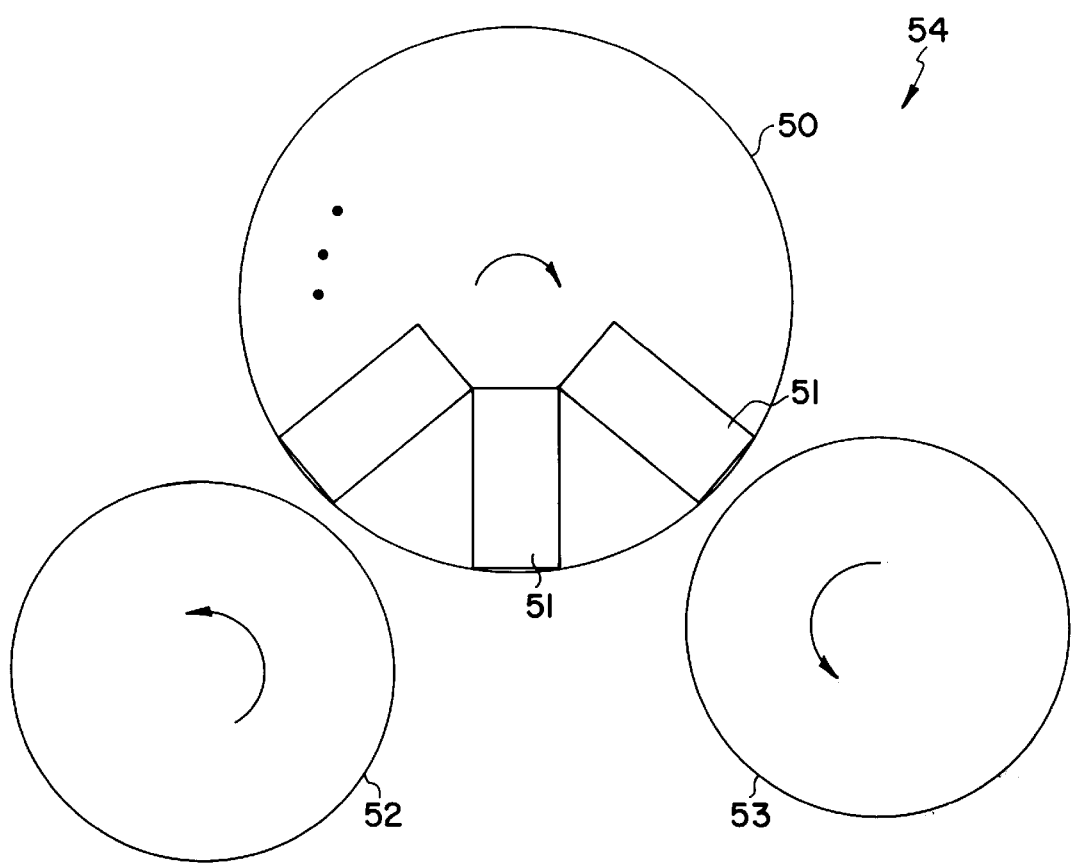
FIG. 6 is a perspective view showing a testing assembly of the detection system according to the present invention.

The testing section 12 further includes at least one testing station 51 and a testing assembly 54 as shown in FIG. 6. Preferably, a rotatable turret assembly 50 containing multiple testing stations 51 is used to test at least several hundred parts per minute. For example, sixteen stations 51 could be provided around the radius of the turret assembly 50. Of course, any suitable number of stations could be used and although FIG. 6 shows a rotating testing assembly, a non-rotating testing assembly could be used to position one or more testing stations 51. In fact, the stations 51 could be mounted at a fixed location and the parts 38 could be fed to and removed from the testing stations 51 by a conveyor, robot or other transfer device.

Each testing station 51 includes upper and lower probes 36 and 37 capable of receiving and holding a testing part 38 therebetween. The probes 36 and 37 are movable toward and away from one another as they rotate on the turret assembly 50. For example, a cam arrangement can be used to vertically reciprocate the probes 36 and 37 relative to one another. In fact, one probe 36 or 37 could be fixedly mounted to the turret assembly 50, while the other probe is movable relative thereto, or both probes 36, 37 could be movable.

When the probes 36 and 37 are spaced apart, an infeed conveyor 52 will place a test part 38 on either probe. As the turret assembly 50 rotates, the probes 36 and 37 are moved toward one another with the part 38 remaining therebetween. Once one or more high voltage spikes are applied to the probes 36 and 37, the probes 36 and 37 can be moved away from one another and the tested part 38 is removed by an outfeed conveyor 53. This testing operation will be described in more detail below.

While it is contemplated that the probes 36 and 37 will be vertically reciprocated relative to one another, they could be horizontally arranged or arranged at an incline. It is merely necessary for the part 38 to be stably held so that it does not fall from the probes 36 and 37 prior or during testing. Of course, some gravity outfeed or infeed arrangement could be used in place of rotating conveyors 52 and 53. Also, a robotic transfer device, linear conveyor such as a belt or chain conveyor, or any other suitable arrangement can be provided for feeding parts 38 to and from the probes 36 and 37.

Figure 5:
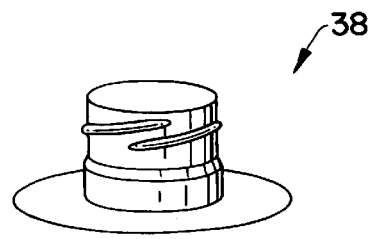
FIG. 5 shows an example of a plastic part tested using the detection system according to the present invention.

The part 38 is made of a non-conductive material, e.g., plastic, rubber, paper, cloth, glass. FIG. 5 shows an example of a testing part 38 made with a plastic, which is used as a cap for beverage containers. The present detection system can test other work pieces having different shapes and configurations.

The detection circuit 14 includes an inductive coupling 39 which inductively senses leakage current from the probe 36 or 37, and an inductive pickup amplifier circuit 40 for amplifying the detected leakage current to generate a detection signal Ds to the PLC circuit 10. The PLC circuit 10 compares the detection signal Ds with a reference signal to generate a test result signal, e.g., "0" (low-level) or "1" (high-level) signal, according to the comparison results. The test result signal is transmitted to the main PLC circuit 16 which directly controls the operation of testing assembly 54. The main PLC circuit 16 includes a larger PLC, e.g., an AB SLC 500 type, which has a scan time of 10–20 ms, but other suitable controllers may be used.

The operation of the high voltage leak detection system according to the present invention is described below. The PLC circuit 10 receives a command from an external source to start the leak detection process. For example, the first optical coupler 22 could receive an external trigger command from the PLC of the main PLC circuit 16. Then the PLC circuit 10 sends a start command to the high voltage generator 31 through, e.g. optical coupler 23. The start command includes one or more pulses, that is, one pulse can be assigned to each work piece, but the PLC 21 can also be programmed to use several pulses per work piece 38. For every pulse received from the PLC circuit 10, the high voltage generator 31 produces a single high voltage spike. The peak level of the voltage spike is adjustable between 10 KV to 20 KV using a variable resistor, but other voltage levels could be used according to the desired performance and output.

As shown in FIG. 6, the testing parts 38 are conveyed through the infeed conveyor 52 rotating in the counterclockwise direction and supplied to a turret assembly 50. The turret assembly 50 has, e.g., sixteen (16) testing stations 51, each testing station 51 including upper and lower probes 36 and 37. As the turret assembly 50 rotates in the clockwise direction, one or more high voltage spikes are applied to each of the testing parts sequentially. The inductive coupling 39 sequentially detects leakage current from the probes of the testing stations 51 to generate detection signals Ds.

The detection signals Ds are received by the monostable trigger circuit 25 which controls the pulse duration of the received signal. Then the detection signals Ds are applied to the PLC 21. The PLC 21 compares the detection signals Ds with a reference signal and generates a test result signal. For example, if the level of detection signal Ds representing leakage current is greater than or equal to the reference signal, then the PLC 21 may generate "1" or a high-level signal, indicating that the part 38 is defective. If the level of detection signal Ds is less than the reference signal, then the PLC 21 may generate "0" or a low-level signal, indicating that the part 38 should not be rejected. Of course, "0" or low-level signal could represent rejection and "1" or high-level signal could represent good part. Also, the detection signal Ds being equal to the reference signal could be analyzed as having a good work piece. Furthermore, the PLC 21 can be programmed to set the reference signal at certain threshold level and the threshold level may be determined depending on the number of voltage spikes applied to each part 38 and detection capabilities of the system.

The PLC 21 sends the test result signal to the PLC of the main PLC circuit 16 through, e.g. optical coupler 24. The main PLC circuit 16 tracts the article (part 38) leaving the testing station 51 from the turret assembly 50 to the outfeed conveyor 53. At an appropriate location, such as on the conveyor 53 or at some downstream location, the main PLC circuit 16 can send a rejection signal to a removing device in or outside the testing assembly 54 to remove the "defective" parts 38 from those other parts 38 which are acceptable and fed to other downstream stations. The device for removing the "defective" part 38 can be an air jet, a scraper arm or any other known means.

Once the parts 38 have been tested, they can be blown out to the outfeed conveyor 53 via air current and are either rejected or maintained based on the leak detection result. The infeed and outfeed conveyors 52 and 53 rotate in a first direction (counterclockwise in FIG. 6) while the turret 50 rotates in an opposite second direction (clockwise in FIG. 6). Of course, these directions could be changed. The infeed conveyor 52, turret assembly 50 with testing stations 51 and outfeed conveyor 53 act as the testing assembly 54.

Since the testing parts are made of a non-conductive material, if there is a hole or leak in the testing part, an electric arc is formed between the upper and lower probes of the testing station. That is, leakage current will be greater than charging current when the part has a leak. However, if there is no hole in the part, then the part functions as an insulator, no electric arc is formed between the probes and the charging current will be greater than the leakage current. The inductive coupling detects leakage current from the part. The detected leakage current is analyzed by the PLC circuit 10 and the test results are transmitted to the main PLC circuit 16. Based on the test results, the main PLC circuit 16 controls the turret assembly of FIG. 6 to either reject or store the testing parts.

The detection system of the present invention is capable of testing more than 320 parts per minute so that at least 300 good parts can be output per minute if twenty parts are found to be defective. Of course, these numbers are exemplary and should not limit the present invention. Air currents may be used to blow the testing parts in and out of the testing stations.

The present invention is advantageous because it detects leaks in work pieces 38 at high speed using high voltage spikes. Further, instead of using direct sensing which can destroy the detection circuit over time, the present invention employs an inductive coupling to indirectly detect leakage current, providing a more reliable and safer detection system.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A system for detecting leakage of an electrically non-conductive part, comprising:

a first controller;

a voltage generating circuit for generating at least one high voltage pulse signal;

at least one testing station including first and second probes for placing a non-conductive part therebetween and for applying said at least one high voltage pulse signal to the non-conductive part; and an inductive detector including an inductive coupling for detecting electrical leakage current from one of said first and second probes, said inductive detector generating a detection signal in response to leakage current and providing said detection signal to said first controller, said first controller comparing the detection signal with a reference signal and determining presence of leaks in non-conductive parts.

2. The system of claim 1, wherein said voltage generating circuit includes a spark gap member coupled between a high voltage generator and said one of said first and second probes.

3. The system of claim 2, wherein said spark gap member includes first and second metal bars having a gap formed therebetween, and a plastic housing containing said first and second metal bars.

4. The system of claim 1, further comprising a testing assembly containing a plurality of said testing stations.

5. The system of claim 4, further comprising a second controller for controlling operation of the testing assembly based on the leakage determination by the first controller.

6. The system of claim 4, wherein said testing assembly includes:

an input conveyor rotatable in a first direction;

a turret having said testing stations, said turret being rotatable in a second direction, said first direction being opposite to the second direction, the parts being transferred from said input conveyor to said testing stations on said turret; and an output conveyor rotatable in the first direction, the parts being transferred from said testing stations on said turret to said output conveyor.

7. The system of claim 6, further comprising a second controller for controlling operation of said input conveyor, said turret, and said output conveyor based on the leakage determination by the first controller.

8. The system of claim 1, wherein said inductive detector includes an amplification circuit for amplifying the detected leakage current to generate the detection signal.

9. The system of claim 1, wherein said voltage generating circuit includes:

a high voltage generator;

a voltage coil; and a variable resistor coupled between said high voltage generator and said voltage coil, a level of said at least one high voltage pulse signal being adjustable by said variable resistor.

10. The system of claim 9, wherein said high voltage generator generates a voltage of about 40 KV.

11. The system of claim 1, wherein said at least one high voltage pulse signal has a voltage level ranging from 10 KV to 20 KV.

12. The system of claim 1, wherein said first controller includes a programmable logic controller (PLC) for comparing the detection signal with the reference signal and generating a test result signal based on said comparison.

13. The system of claim 1, wherein said first controller includes a monostable trigger circuit and a plurality of optical couplers.

14. A method for detecting leakage of an electrically non-conductive part, comprising the steps of:

generating at least one high voltage pulse signal;

applying said at least one high voltage pulse signal to a non-conductive part positioned between first and second probes of at least one testing station;

measuring the amount of electrical coupling by inductively detecting electrical leakage current from one of the first and second probes and generating a detection signal; and comparing the detection signal with a reference signal to detect leaks in non-conductive parts.

15. The method of claim 14, wherein said step of generating at least one high voltage pulse signal further includes the step of visually indicating generation of said at least one high voltage pulse signal.

16. The method of claim 15, wherein in said visually indicating step, an electric arc between metal bars of a spark gap member is used as a visual indicator.

17. The method of claim 14, wherein said step of generating at least one high voltage pulse signal includes the step of adjusting the level of said at least one high voltage pulse signal using a variable resistor.

18. The method of claim 14, wherein said step of generating at least one high voltage pulse signal includes the step of generating a voltage pulse signal having a voltage level ranging from 10 KV to 20 KV.

19. The method of claim 14, wherein said comparing step includes the step of controlling a pulse duration of the detection signal.

20. The method of claim 14, wherein said applying step includes the steps of:

providing a turret having a plurality of said testing stations, each testing station having first and second probes;

moving the parts to the testing stations using an input conveyor; and moving the parts away from the testing stations using an output conveyor.

* * * * *